(12) United States Patent
DiBiasio et al.

(10) Patent No.: US 10,071,193 B2
(45) Date of Patent: *Sep. 11, 2018

(54) COMPACT HYDRAULIC MANIFOLD STRUCTURE FOR SHEAR SENSITIVE FLUIDS

(71) Applicant: The Charles Stark Draper Laboratory, Inc., Cambridge, MA (US)

(72) Inventors: Christopher DiBiasio, Stoughton, MA (US); Joseph L. Charest, Cambridge, MA (US); Jeffrey T. Borenstein, Newton Upper Falls, MA (US); Ernest Kim, Cambridge, MA (US); Daniel I. Harjes, Acton, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 59 days.

This patent is subject to a terminal disclaimer.

(21) Appl. No.: 15/094,623

(22) Filed: Apr. 8, 2016

(65) Prior Publication Data
US 2016/0220961 A1    Aug. 4, 2016

Related U.S. Application Data

(63) Continuation of application No. 13/604,256, filed on Sep. 5, 2012, now Pat. No. 9,421,315.

(51) Int. Cl.
*B01D 63/08* (2006.01)
*B01D 63/00* (2006.01)
(Continued)

(52) U.S. Cl.
CPC ............... *A61M 1/34* (2013.01); *A61M 1/16* (2013.01); *A61M 1/1631* (2014.02);
(Continued)

(58) Field of Classification Search
CPC .. B01D 63/081; B01D 63/082; B01D 63/084; B01D 63/085; B01D 63/087;
(Continued)

(56) References Cited

U.S. PATENT DOCUMENTS 2,734,224 A    4/1953  Winstead
3,074,559 A *  1/1963  Savino ................... B01D 61/28
                                                    128/DIG. 3
(Continued)

FOREIGN PATENT DOCUMENTS

DE         68 01 138 U      3/1969
WO    WO-2008/127732 A2    10/2008
(Continued)

OTHER PUBLICATIONS

Notice of Allowance dated Apr. 19, 2016 in U.S. Appl. No. 13/604,256 (10 pages).
(Continued)

*Primary Examiner* — Pranav N Patel
(74) *Attorney, Agent, or Firm* — Christopher J. McKenna; Foley & Lardner LLP

(57) ABSTRACT

A compact hydraulic manifold for transporting shear sensitive fluids is provided. A channel network can include a trunk and branch architecture coupled to a bifurcation architecture. Features such as tapered channel walls, curvatures and angles of channels, and zones of low fluid pressure can be used to reduce the size while maintaining wall shear rates within a narrow range. A hydraulic manifold can be coupled to a series of microfluidic layers to construct a compact microfluidic device.

8 Claims, 6 Drawing Sheets

(51) Int. Cl.
- *A61M 1/34* (2006.01)
- *F17D 1/00* (2006.01)
- *A61M 1/16* (2006.01)
- *B01D 61/24* (2006.01)
- *B01L 3/00* (2006.01)

(52) U.S. Cl.
CPC ......... *B01D 61/243* (2013.01); *B01D 63/005* (2013.01); *B01D 63/082* (2013.01); *B01D 63/085* (2013.01); *B01D 63/088* (2013.01); *B01L 3/5027* (2013.01); *F17D 1/00* (2013.01); *A61M 1/1698* (2013.01); *A61M 2202/0413* (2013.01); *A61M 2205/0244* (2013.01); *A61M 2205/75* (2013.01); *B01D 2313/08* (2013.01); *B01D 2313/105* (2013.01); *B01D 2319/04* (2013.01); *B01L 2300/0864* (2013.01); *B01L 2300/0874* (2013.01); *Y10T 137/794* (2015.04)

(58) Field of Classification Search
CPC .......... B01D 2313/08; B01D 2313/086; B01D 2313/19; B01D 69/06; B01D 69/10; B01D 61/24–61/32; B01D 63/08–63/088; B01D 29/0004; B01D 29/0095; B01D 29/05; B01D 2313/10–2313/125; B01D 2313/14–2313/146; B01D 2313/20; B01D 2315/10; B01D 2315/16; C02F 1/442; C02F 1/444
See application file for complete search history.

(56) References Cited

U.S. PATENT DOCUMENTS

| | | |
|---|---|---|
| 3,585,131 A | 6/1971 | Esmond |
| 3,695,445 A | 10/1972 | Esmond |
| 4,110,220 A | 8/1978 | Lavender |
| 4,980,054 A | 12/1990 | Lavender |
| 2002/0036018 A1 | 3/2002 | McNeely et al. |
| 2002/0182241 A1 | 12/2002 | Borenstein et al. |
| 2003/0039169 A1 | 2/2003 | Ehrfeld et al. |
| 2003/0150806 A1 | 8/2003 | Hobbs et al. |
| 2005/0020557 A1 | 1/2005 | Johnson et al. |
| 2005/0167354 A1 | 8/2005 | Caze et al. |
| 2005/0202557 A1 | 9/2005 | Borenstein et al. |
| 2006/0136182 A1 | 6/2006 | Vacanti et al. |
| 2008/0093298 A1 | 4/2008 | Browning et al. |
| 2008/0251444 A1 | 10/2008 | Fendya et al. |
| 2009/0181200 A1 | 7/2009 | Borenstein et al. |
| 2009/0234266 A1 | 9/2009 | Solomon et al. |
| 2009/0269837 A1 | 10/2009 | Shevkoplyas et al. |
| 2009/0316972 A1 | 12/2009 | Borenstein et al. |
| 2010/0234678 A1 | 9/2010 | Pryor et al. |
| 2010/0267136 A1 | 10/2010 | Vacanti et al. |
| 2010/0274353 A1 | 10/2010 | Pryor et al. |
| 2010/0326916 A1 | 12/2010 | Wrazel et al. |
| 2011/0155667 A1 | 6/2011 | Charest et al. |
| 2011/0290113 A1 | 12/2011 | Borenstein et al. |
| 2011/0296903 A1 | 12/2011 | Cao et al. |

FOREIGN PATENT DOCUMENTS

| | | |
|---|---|---|
| WO | WO-2011/059786 A1 | 5/2011 |
| WO | WO-2011/150216 A1 | 12/2011 |

OTHER PUBLICATIONS

International Preliminary Report on Patentability dated Jul. 23, 2015 in PCT Application No. PCT/US2014/010440.
International Preliminary Report on Patentability dated Mar. 19, 2015 in PCT Application No. PCT/US2013/057842.
International Search Report and Written Opinion dated Apr. 16, 2014 in PCT Application No. PCT/US2014/010440.
International Search Report and Written Opinion dated May 21, 2015 in PCT Application No. PCT/US2015/016171.
International Search Report and Written Opinion dated Oct. 23, 2013 in PCT Application No. PCT/US2013/057842 (13 pages).
Office Action issued in European Patent Application No. 13765553.6 dated Feb. 23, 2016.
U.S. Notice of Allowance for U.S. Appl. No. 13/604,256 dated Feb. 16, 2016.
U.S. Notice of Allowance for U.S. Appl. No. 13/604,256 dated Jan. 20, 2016.
U.S. Office Action for U.S. Appl. No. 13/604,256 dated Oct. 23, 2015.
U.S. Office Action for U.S. Appl. No. 13/736,685 dated Mar. 3, 2016.
U.S. Office Action for U.S. Appl. No. 13/736,685 dated Sep. 4, 2015.
U.S. Office Action in U.S. Appl. No. 13/604,256 dated Nov. 18, 2014.
U.S. Office Action dated Feb. 12, 2014 in U.S. Appl. No. 13/604,256 (21 pages).
U.S. Office Action on U.S. Appl. No. 13/604,256 dated Apr. 6, 2015.
European Patent Office Examination Report for Application No. 14704937.3 dated Jun. 22, 2017.
U.S. Notice of Allowance on U.S. Appl. No. 13/604,256 dated Apr. 19, 2016.
U.S. Notice of Allowance on U.S. Appl. No. 13/736,685 dated Jun. 22, 2016.
U.S. Notice of Allowance on U.S. Appl. No. 14/624,247 dated Jun. 16, 2017.
U.S. Office Action on U.S. Appl. No. 14/624,247 dated Mar. 30, 2017.
U.S. Office Action on U.S. Appl. No. 14/624,247 dated Nov. 1, 2016.
U.S. Office Action on U.S. Appl. No. 15/601,376 dated Jul. 13, 2017.

* cited by examiner

COMPACT HYDRAULIC MANIFOLD STRUCTURE FOR SHEAR SENSITIVE FLUIDS

CROSS-REFERENCE TO RELATED PATENT APPLICATIONS

The present application is a continuation of, and claims priority to and the benefit of, U.S. patent application Ser. No. 13/604,256, filed Sep. 5, 2012, now U.S. Pat. No. 9,421,315, which issued on Aug. 23, 2016, and is incorporated herein by reference in its entirety.

BACKGROUND

The wall shear rate for blood travelling through a network of channels must be maintained within a limited range to preserve blood health. Shear rates outside of the acceptable range can lead to clotting or hemolysis. Blood health is important in organ assist devices, which often contain channels carry blood. Patient mobility can also be an important factor in the success of an organ assist device. It is therefore desirable to have a compact channel network architecture that is capable of safely transporting blood and other shear sensitive fluids.

SUMMARY OF THE INVENTION

Aspects and implementations of the present disclosure are directed to a compact hybrid hydraulic manifold structure for shear sensitive fluids.

At least one aspect is directed to a microfluidic device. The microfluidic device includes a first network of channels having a plurality of First Channels. Each First Channel has a height in the range of about 50 microns to about 500 microns, a width in the range of about 50 microns to about 1.5 millimeters, and a length in the range of about 3 centimeters to about 20 centimeters. The microfluidic device includes a second network of channels having at least one Second Channel complementary to one or more of the First Channels. The microfluidic device includes a filtration membrane separating the one or more First Channels from the at least one Second Channel. The plurality of First Channels includes an input channel forming a primary channel, a plurality of secondary channels, and an outlet channel. A first secondary channel connects to the primary channel at a first junction located at a first distance along the primary channel. A second secondary channel connects to the primary channel at a second junction located at a second distance, greater than the first distance, along the primary channel. The primary channel and the first and second secondary channels are configured such that flow of fluid through the primary channel beyond the first junction is substantially greater than flow of fluid into the first secondary channel In some implementations, the plurality of First Channels is located within a first substrate. The first substrate can have a thickness in the range of about 10 microns to about 10 millimeters.

In some implementations, at least one of the first and second secondary channels of the microfluidic device bifurcates into first and second tertiary channels at a third junction, such that a fluid flow rate through the first tertiary channel is substantially the same as a fluid flow rate through the second tertiary channel, and the total fluid flow rate between the first and second tertiary channels is substantially the same as the fluid flow rate through the portion of the at least one secondary channel between the primary channel and the third junction.

In some implementations, the microfluidic device includes a flow divider for dividing fluid flow between the first and second tertiary channels. The flow divider has a curved surface connecting to the walls of the first and second tertiary channel, and the radius of curvature of the flow divider is not greater than the hydraulic diameter of the at least one secondary channel. In some implementations, the microfluidic device includes third and fourth tertiary channels that converge at a point where they have opposing curvatures to form a third secondary channel, such that all of the fluid flowing through the third and fourth tertiary channels is subsequently transported into the third secondary channel.

In some implementations, the diameter of at least one secondary channel at a portion adjacent to its junction with the primary channel is significantly greater than the diameter of the downstream portion of the at least one secondary channel, such that a zone of low fluid pressure is created at the junction. In some implementations, an angle formed by a centerline of the secondary channel and a downstream portion of the centerline of the primary channel measures in the range of about one to about sixty degrees. In some implementations, the channels are further configured to maintain a shear rate of within a range of about two hundred inverse seconds to about two thousand inverse seconds when blood is transported through the channels. In some implementations, the walls of the primary channel are disposed at an angle of no greater than thirty degrees with respect to the direction of fluid flow through the primary channel.

In some implementations, at least one secondary channel includes a curved portion directing flow away from the primary channel. In some implementations, the curved portion of the at least one secondary channel has a radius of curvature that is not less than its hydraulic diameter.

At least one aspect is directed to a microfluidic device. The microfluidic device includes a first manifold having a primary inlet channel and a plurality of secondary inlet channels, coupled to a first plurality of substrates each having a network of First substrate channels. The microfluidic device includes a plurality of second substrates. Each second substrate corresponds to one of the first substrates and includes at least one Second channel complementary to one or more of the First substrate channels. The microfluidic device includes a plurality of filtration membranes. Each filtration membrane separates the First Channels of one of the plurality of first substrates from the at least one Second channel included in a corresponding second substrate. Each of the First substrate channels has a height in the range of about 50 microns to about 500 microns, a width in the range of about 50 microns to about 1.5 millimeters, and a length in the range of about 3 centimeters to about 20 centimeters. A first secondary inlet channel connects to the primary inlet channel at a first junction located at a first distance along the primary inlet channel. A second secondary inlet channel connects to the primary inlet channel at a second junction located at a second distance, greater than the first distance, along the primary inlet channel. The inlet channels are configured such that flow of fluid through the primary inlet channel beyond the first junction is substantially greater than flow of fluid into the first secondary inlet channel.

In some implementations, the network of First substrate channels in at least one of the first plurality of substrates comprises a primary substrate channel and a plurality of secondary substrate channels. The microfluidic device includes a first secondary substrate channel connecting to the primary substrate channel at a first junction located at a first distance along the primary substrate channel. The microfluidic device includes a second secondary substrate channel connecting to the primary substrate channel at a second junction located at a second distance, greater than the first distance, along the primary substrate channel. The substrate channels in the microfluidic device are configured such that flow of fluid through the primary substrate channel beyond the first junction is substantially greater than flow of fluid into the first secondary substrate channel.

In some implementations, the microfluidic device includes a second manifold having a primary inlet channel and a plurality of secondary inlet channels, coupled to a second plurality of substrates each having a network of Second substrate channels. The microfluidic device includes a first secondary inlet channel connecting to the primary inlet channel at a first junction located at a first distance along the primary inlet channel. The microfluidic device includes a second secondary inlet channel connecting to the primary inlet channel at a second junction located at a second distance, greater than the first distance, along the primary inlet channel. The network of secondary channels of each of the second plurality of substrates connects to a secondary inlet channel at a junction such that fluid can be transported from the second manifold to the network of Second substrate channels of each of the second plurality of substrates.

In some implementations, each of the second plurality of substrates is coupled to a respective one of the first plurality of substrates to form a bilayer. In some implementations, an angle formed by a surface of at least one of the first plurality of substrates and the downstream portion of the primary inlet of the first manifold is in the range of about one to about sixty degrees.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

DESCRIPTION OF CERTAIN ILLUSTRATIVE IMPLEMENTATIONS

Following below are more detailed descriptions of various concepts related to, and implementations of, a compact hydraulic manifold structure for shear sensitive fluids. The various concepts introduced above and discussed in greater detail below may be implemented in any of numerous ways, as the described concepts are not limited to any particular manner of implementation. Examples of specific implementations and applications are provided primarily for illustrative purposes.

Figure 1A:
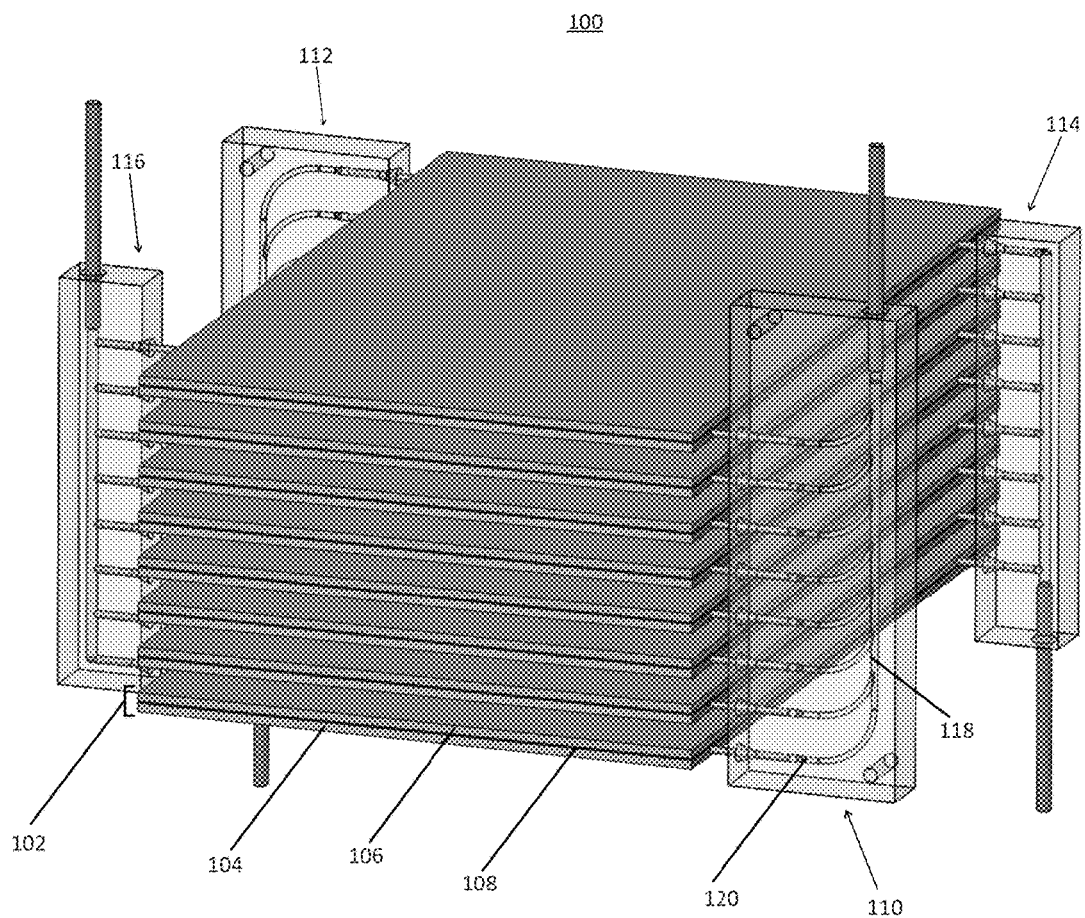
FIG. 1A is a depiction of a first microfluidic device according to an illustrative implementation.

FIG. 1A depicts a microfluidic device 100 composed of eight bilayers, as exemplified by the bilayer 102. Each bilayer 102 consists of a blood substrate layer, such as the blood substrate layer 104, and a filtrate substrate layer, such as the filtrate substrate layer 106, separated by a permeable membrane, such as the permeable membrane 108. A network of channels within the blood substrate 104 and the filtrate substrate 106 allows fluid (i.e. blood or filtrate) to be transported. The microfluidic device 100 also includes a blood inlet manifold 110 and a blood outlet manifold 112, both coupled to the blood substrate layer 104. Similarly, a filtrate inlet manifold 114 and a filtrate outlet manifold 116 are coupled to the filtrate substrate layer 106. Blood enters the blood substrate layer 104 through the blood inlet manifold 110 and exits through the blood outlet manifold 112. Filtrate enters the filtrate substrate layer 106 through the filtrate inlet manifold 114 and exits through the filtrate outlet manifold 116.

Figure 1B:
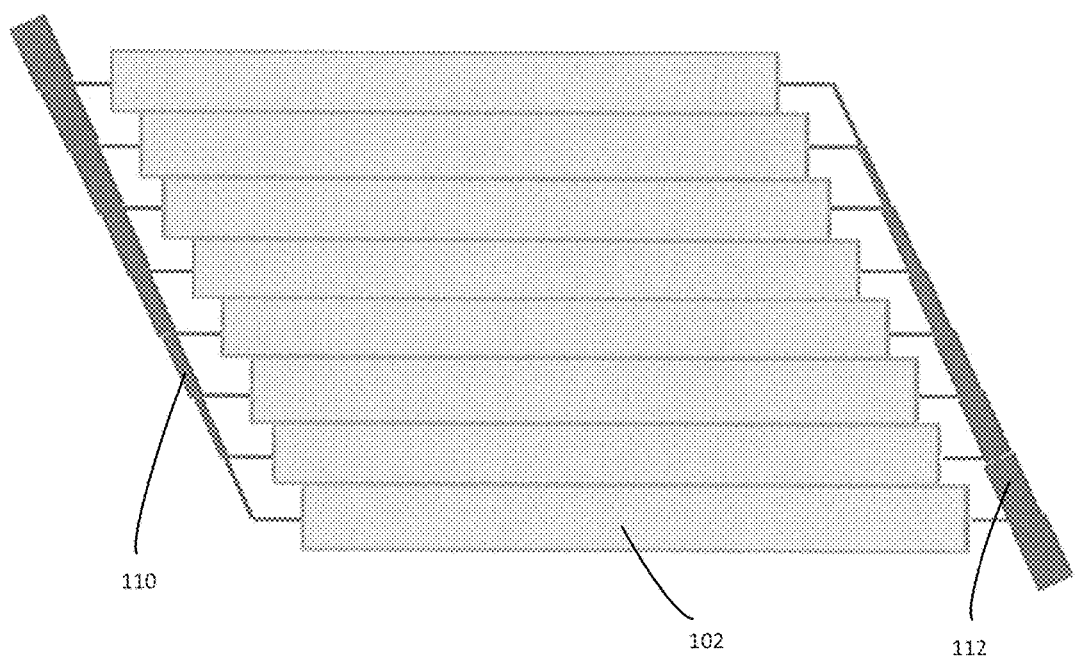
FIG. 1B is a depiction of a second microfluidic device according to an illustrative implementation.

In one implementation, each bilayer 102 is parallel to each other bilayer 102, as shown in FIG. 1A. Although FIG. 1A depicts the bilayers 102 as perpendicular relative to the manifolds 110, 112, 114, and 116, this orientation is not essential. For example, FIG. 1B shows an alternative arrangement, in which the blood inlet manifold 110 and the blood outlet manifold 112 are not perpendicular to the bilayers 102. This configuration reduces the angle through which the blood flows as it enters into the blood inlet manifold 110, flows through the bilayer 102, and exits through the blood outlet manifold 112. The blood substrate layer 104 and the filtrate substrate layer 106 each have a thickness in the range of about 10 microns to about 10 millimeters, and the membrane 108 has thickness in the range of about 500 nanometers to about 1 millimeter. In some implementations, adjacent bilayers 102 can be in contact with one another. In other implementations, the bilayers 102 can be separated by a distance of about 500 microns or more, as shown in FIG. 1.

The device 100 is designed for use in hemofiltration. The network of channels within the blood substrate layer 104 and the filtrate substrate layer 106 divide the fluid (i.e. blood and filtrate) so that a relatively large surface area of each fluid is exposed to the permeable membrane 108. Each channel of the blood substrate layer 104 is aligned with a corresponding channel of the filtrate substrate layer 106, so that the corresponding channels are separated by the permeable membrane 108. As the blood moves through the channels of the blood substrate layer 104, filtrate moves in the opposite direction through the filtrate substrate layer 106 and waste products and water are removed from the blood via diffusion through the permeable membrane 108 into the filtrate substrate layer 106. Healthy blood remains in the blood substrate layer 104 and can then be recirculated into the body of a patient.

The blood inlet manifold 110 has a primary channel 118 coupled to several secondary channels, as exemplified by the secondary channel 120. The other manifolds 112, 114, and 116 have primary and secondary channels similar to the primary channel 118 and secondary channel 120. Features of the blood manifolds 110 and 112, such as the curved shape of the channels, help to preserve blood health. These features are described further below. The shape of the filtrate manifolds 114 and 116 are less important, because filtrate is typically not a shear sensitive fluid like blood.

The blood substrate layer 104 and the filtrate substrate layer 106 can be made of a thermoplastic, such as polystyrene, polycarbonate, polyimide, or cyclic olefin copolymer (COC), biodegradable polyesters, such as polycaprolactone (PCL), or soft elastomers such as polyglycerol sebacate (PGS). The substrate layers 104 and 106 may alternatively be made of polydimethylsiloxane (PDMS), poly(N-isopropylacrylamide), or nanotubes or nanowires formed from, for example, carbon or zinc oxide. The substrates 104 and 106 are made of an insulating material to maintain temperature stability. In some implementations, the channels can be coated with cytophilic or cytophobic materials to promote or prevent the growth of cells, such as vascular endothelial cells, in the channels. The channels may also be coated with an anticoagulant to help prevent clotting of the blood in the blood substrate layer 104.

Figure 2:
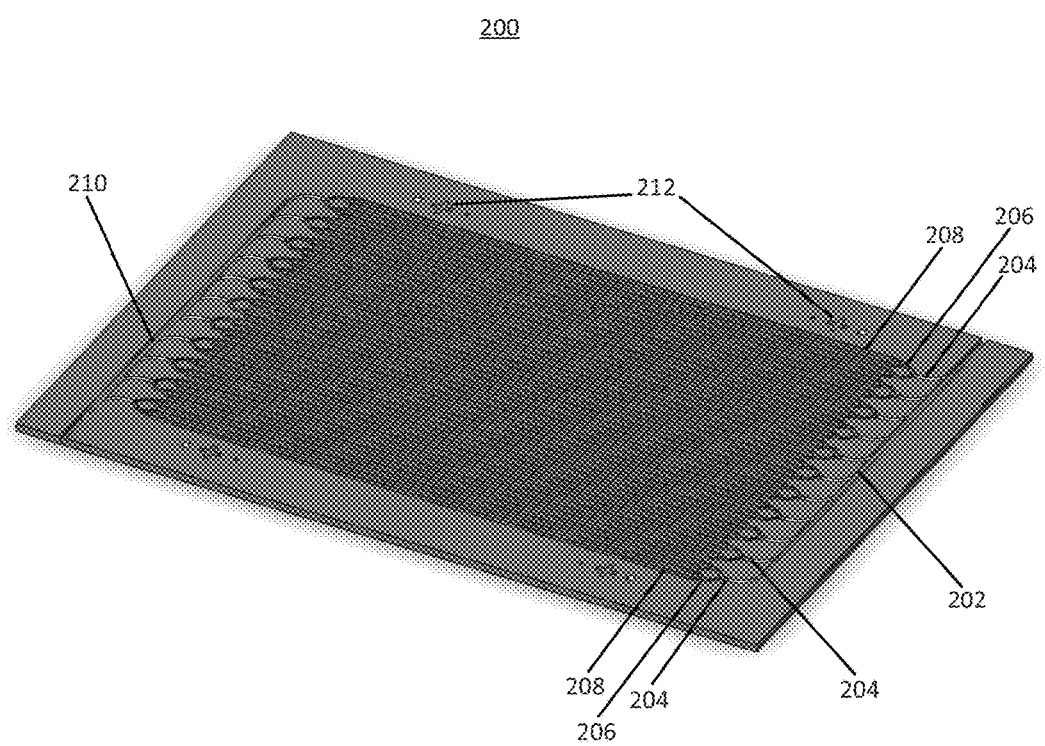
FIG. 2 is a depiction of a single substrate layer that can be used in the microfluidic device of FIG. 1A or FIG. 1B, according to an illustrative implementation.

FIG. 2 illustrates a blood substrate layer 200 suitable for use as the blood substrate layer 104 of FIG. 1A. The blood substrate layer 200 has a network of channels, which includes a primary channel 202, secondary channels such as channel 204, tertiary channels such as channel 206, quaternary channels such as channel 208, and an outlet channel 210. The blood substrate layer 200 has a thickness in the range of about 10 microns to 10 millimeters. In some implementations, each channel has a height in the range of about 10 microns to about 1 millimeter and a width in the range of about 50 microns to about 1.5 millimeters. In some implementations, the width of each channel is less than about 900 microns.

As used herein, the term "height" refers to the greatest depth of each channel. The term "width" refers to the greatest distance between interior edges of a channel, as measured in a direction perpendicular to the flow of fluid and within the plane occupied by the substrate layer containing the channel. In some implementations, each channel can have a substantially semi-circular cross-section. In other implementations, the channels may have rectangular or trapezoidal cross sections. In still other implementations, the cross sections of the channels can be irregular in shape. For example, the channel may be generally rectangular with rounded or faceted corners. Each channel is created by etching, milling, stamping, plating, direct micromachining, or injection molding. The top portions of the channels on the blood substrate layer 200 are open and do not include a top wall. In the final configuration of the microfluidic device 100 shown in FIG. 1A, the permeable membrane 108 will be placed in contact with the blood substrate layer 200 to form enclosed channels.

The blood substrate layer 200 also includes alignment features 212 to facilitate alignment of the blood substrate layer 200 with the permeable membrane 108 and the filtrate substrate layer 106 of FIG. 1A to form a bilayer, such as the bilayer 102. This can ensure the correct orientation of the blood substrate layer 200 with respect to the permeable membrane 108 and the filtrate substrate layer 106. Characteristics of the network of channels in the blood substrate layer are further discussed below.

Figure 3:
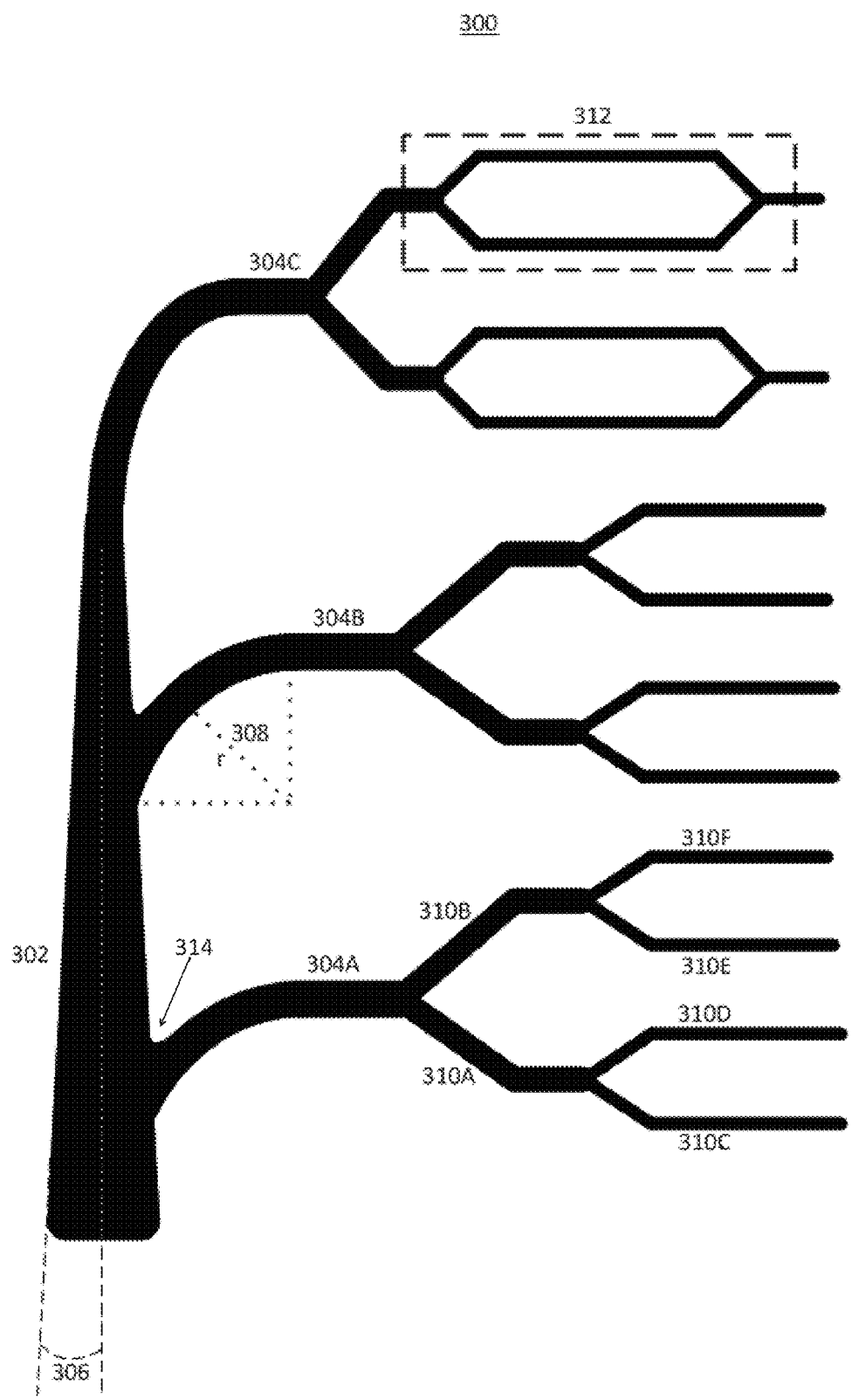
FIG. 3 is a schematic view of a network of channels.

FIG. 3 depicts a network of channels 300. The network of channels 300 includes a trunk channel 302, branch channels 304A-304C, and bifurcation channels 310A-310F. In one implementation, portions of the network of channels 300 represent the network of channels within the blood substrate layer 200 shown in FIG. 2. For example, the trunk 302 of FIG. 3 can correspond to the primary channel 202 of FIG. 2, the branch channel 304A can correspond to the secondary channel 204, the bifurcation channel 310A can correspond to the tertiary channel 206, and the bifurcation channel 310C can correspond to the quaternary channel 208. In another implementation, the network of channels 300 represents the channels in the blood inlet manifold 110 and the blood outlet manifold 112 of FIG. 1A. For example, the trunk 302 can represent the primary channel 118 and the branch 304C can represent the secondary channels 120. In this example, each branch 304A-304C couples to a single blood substrate layer 104 of FIG. 1A. Generally, the network of channels 300 would not need to be used for the filtrate inlet manifold 114, the filtrate substrate layer 106, or the filtrate outlet manifold 116 because filtrate is not a shear sensitive fluid. In some implementations, in which the blood inlet manifold 110 includes a trunk channel and branch channels similar to the trunk 302 and branch channels 304A-304C, the branch channels couple to the primary channel of a blood substrate layer. The primary channels of the blood substrate layers then branches into secondary and tertiary channels.

In one implementation, a volume of fluid enters the trunk 302 at its widest point. As the fluid travels along the trunk 302, a portion of the fluid is redirected through the branch channels 304A-304C. Although only three branch channels 304A-304C are shown in FIG. 3, it should be appreciated that the network of channels 300 is illustrative only, and that the trunk 302 may be coupled to any number of the branch channels 304. In some implementations, the trunk 302 couples to additional branch channels (not shown in FIG. 3) on other sides of the trunk 302. Such additional channels can branch off the trunk 302 on the same side or opposite side of the trunk 302 as the branch channels 304A-304C.

The channels are configured such that the volume of fluid redirected into a single branch channel 304 (other than the last branch channel, i.e. branch channel 304C) is significantly less than the total volume of fluid flowing through the trunk 302 at the point at which the branch 304 meets the trunk 302. For example, as fluid enters the widest portion of the trunk 302 and travels along the trunk 302, a relatively small percentage of the fluid is redirected into the first branch channel 304A. In various implementations, the percentage of fluid diverted into the branch channel 304A is less than 50%, less than 40%, less than 30%, less than 20%, or less than 10% of the total fluid at the junction. A larger percentage of the fluid continues to flow through the trunk 302 and is then redirected into the branch channels 304B-304C. The percentage redirected is a function of the number of branch channels and is controlled by varying the dimensions of each branch channel.

These flow characteristics are achieved by selecting hydraulic diameters for the branch channels 304A-304C that are significantly smaller than the hydraulic diameter of the trunk 302. The hydraulic diameters of the branch channels 304A-304C may not necessarily be equal. In one example, the hydraulic diameters of the trunk 302 and the branch channels 304A-304C are selected according to Murray's Law. Murray's Law provides a technique for selecting the radius of channels in a network in order to balance the energy required to circulate fluid (e.g. blood) and the energy required to metabolically support the fluid. Generally, Murray's Law indicates that for a primary channel having a radius of $r_p$ and branch channels having radii of $r_{b1}$, $r_{b2}$, etc., the relationship between the radii of all of the channels should be:

$r_p^3 = r_{b1}^3 + r_{b2}^3 + \ldots + r_{bn}^3$. Murray's Law can also be used to select the relationships between the hydraulic diameters of a primary channel and branch channels in a network with non-circular cross sections. For example, for a primary channel having a hydraulic diameter $d_p$ and branch channels having hydraulic diameters of $d_{b1}$, $d_{b2}$, etc., Murray's Law indicates that the relationship between the hydraulic diameters of all of the channels should be:

$$(dp1/2)^3 = (db1/2)^3 + (db2/2)^3 + \ldots + (dbn/2)^3$$

In some implementations, and as shown in FIG. 3, the diameter of the trunk 302 is varied along its length to adhere to Murray's Law. The variation of the diameter is smooth, giving the trunk 302 a tapered shape in the direction of fluid flow. In some implementations, the angle 306 formed by the centerline of the trunk 304 (i.e., the direction of fluid flow through the trunk 304) and the tapered wall of the trunk 304 is less than about 45°. In some implementations, the angle 306 is less than about 30°. In some implementations, the angle 306 is less than about 20°. Other walls of the trunk may also be tapered (e.g., the trunk may have a tapered height instead of, or in addition to, a tapered width).

The branch channels 304A-304C are coupled to the trunk 302 and are used to carry fluid in a direction away from the trunk 302. In some implementations, the branch channels 304A-304C are straight channels. In other implementations, the branch channels 304A-304C curve away from the trunk 302, as shown in FIG. 3. Curvature of the branch channels 304A-304C allows for smoother fluid flow and helps to maintain wall shear rate within an acceptable range. The radius of curvature 308 of the branch channels 304A-304C also affects the shear rate of fluid flowing through the network of channels 300. The network of channels 300 is configured such that the radius of curvature 308 of each branch channel 304A-304C is no less than the hydraulic diameter of the corresponding branch channel 304A-304C.

The network of channels 300 also includes bifurcations, as illustrated by bifurcation channels 310A-310F. A bifurcation channel directs fluid flow from a first channel (e.g., branch channel 304A) into one of two additional channels (e.g. bifurcation channels 310A and 310B). The bifurcation channels 310A-310F are configured to substantially evenly split the fluid flow from the channels to which they are coupled. For example, branch channel 304A and bifurcation channels 310A and 310B are configured such that the fluid flow rate through bifurcation channel 310A is substantially the same as the fluid flow rate through bifurcation channel 310B, and the total fluid flow rate through bifurcation channels 310A and 310B is the same as the fluid flow rate through branch channel 304A. In some implementations, the bifurcation channels are designed in accordance with Murray's Law. For example, the cube of the radius of branch channel 304A can be selected to equal the sum of the cubes of the radii of bifurcation channels 310A and 310B.

A flow divider 314, formed by the junction of the trunk 302 and the branch 304A, has a rounded surface, as shown in FIG. 3. The rounded surface of the flow divider 314 helps to maintain smooth fluid flow through the trunk 302 and the branch channel 304A. In some implementations, the radius of curvature of the flow divider 314 is no greater than the hydraulic diameter of the portion of the trunk 302 proximate to the flow divider. The flow divider feature is described further below in connection with FIG. 4.

The network of channels 300 can contain any number of bifurcations. In some implementations, there are multiple bifurcations in a single path through the network of channels 300. For example, the fluid flow through the branch channel 304A bifurcates into bifurcation channels 310A and 310B, and then further bifurcates into the bifurcation channels 310C-310F. Fluid flow can also be recombined after a bifurcation, as shown in a bifurcation subnetwork 312 depicted at the top of FIG. 3.

The features described above, such as the taper of the trunk 302, the curvature of the branches 304A-304C, and the bifurcation channels 310A-310F, are selected to maintain a wall shear rate within a specified range substantially throughout the entire channel network 300. In a device that will be used to transport blood, such as the microfluidic device 100 of FIG. 1A or the blood substrate layer 200 of FIG. 2, the features of the channel network 300 can be selected to maintain a wall shear rate in the range of about 200 $s^{-1}$–2000 $s^{-1}$. In other implementations, the channel network 300 can be designed to allow for shear rate ranges outside of this range. Additional features that can be used to maintain blood health are further described below in connection with FIG. 4 and FIG. 5.

The selection of features described above in connection with FIG. 3 for use in a microfluidic device can be optimized for various applications. For example, the bifurcation channels 310A-F are useful for maintaining wall shear rate and smooth fluid flow, but multiple bifurcations will occupy a relatively large volume of space, requiring a large overall device size. Coupling a bifurcation network, such as the bifurcation channels 310A-310F, to a trunk and branch network, such as the trunk 302 and the branch channels 304A-304C, results in a smaller overall device while preserving wall shear rates within an acceptable range throughout.

The direction of fluid flow in the examples described above is illustrative only. For example, the channel network 300 could be used to transport fluid first through the bifurcation channels 310A-310F, then into the branch channel 304A, and finally into the trunk 302. Further, the features depicted in FIG. 3 and described above may apply to any type of channel in the channel network 300. For example, although FIG. 3 shows a taper only along the trunk 302, any other channel in the network 300 can also be tapered. Similarly, the curved structure shown on the branch channels 304A-304C could be applied to any other channel in the network 300, such as the trunk 302 or the bifurcations 310A-310F.

Figure 4:
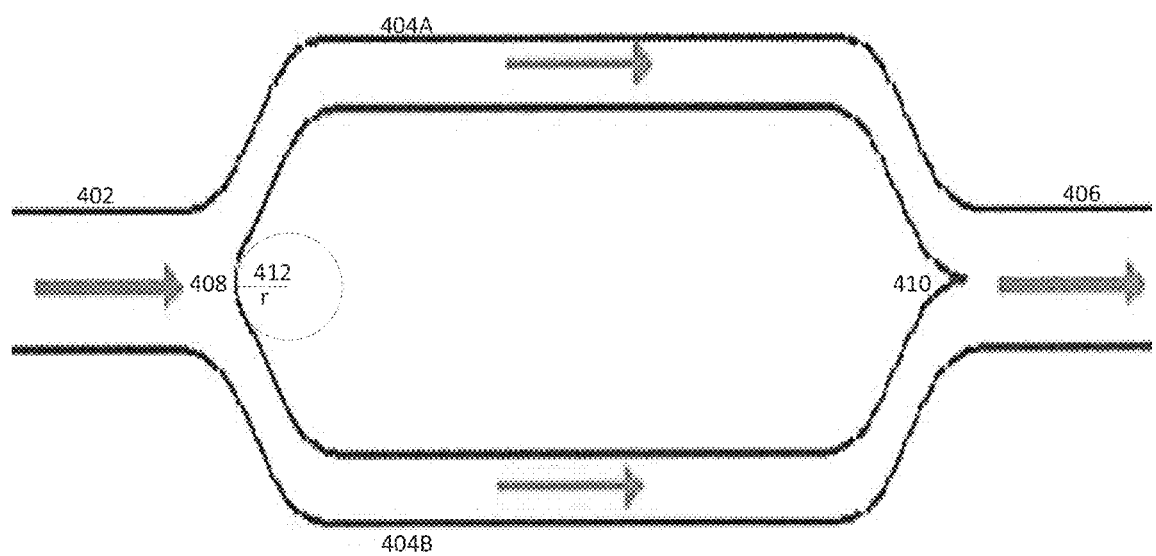
FIG. 4 is an enlargement of a portion of the network of channels shown in FIG. 3.

FIG. 4 depicts a bifurcation network of channels 400 for dividing and recombining fluid flow, similar to the bifurcation subnetwork 312 of FIG. 3. The bifurcation network 400 includes an inlet channel 402, bifurcation channels 404A-404B, and an outlet channel 406. The bifurcation network 400 also includes a flow divider 408 for dividing the fluid flow from the inlet channel 402 into the bifurcation channels 404A-404B, and a convergence point 410 for recombining the fluid flow from the bifurcation channels 404A-404B into the outlet channel 406.

The flow divider 408 is formed by the junction of the walls of the bifurcation channels 404A-404B. Fluid traveling through the inlet channel 402 is redirected into either the bifurcation channel 404A or the bifurcation channel 404B by the flow divider 408. The flow divider 408 and the bifurcation channels 404A-404B are configured to substantially evenly divide the total fluid flow from the inlet channel 402 into the bifurcation channels 404A and 404B. In some implementations, the walls of the bifurcation channels 404A and 404B join at a sharp point, such that the radius of curvature 412 of the flow divider 408 is effectively zero. In other implementations, the flow divider 408 has a rounded surface connecting to the walls of the bifurcation channels 404A and 404B to allow fluid to flow more uniformly into the bifurcation channels 404A-404B. In some implementations, the flow divider 408 is designed with a radius of curvature 408 that is no greater than the hydraulic diameter of the inlet channel 402. This helps to maintain even flow and keeps the shear rate within a specified range for a shear sensitive fluid, such as blood.

Fluid flow through the bifurcation channels 404A and 404B is recombined into the outlet channel 406 at the convergence point 410, defined by the downstream junction of the walls of the bifurcation channels 404A and 404B. In some implementations, the bifurcation channels 404A and 404B each have substantially straight walls at the convergence point 410. In other implementations, the bifurcation channels 404A and 404B are curved at the convergence point 410. For example, the bifurcation channels 404A and 404B shown in FIG. 4 have opposing curvatures at the convergence point 410. Like the curved flow divider 408, opposing curvatures at the convergence point 410 reduce eddie currents and vortices and maintain shear rate within a specified range, which promotes blood health when the channels are used in an medical device.

Figure 5:
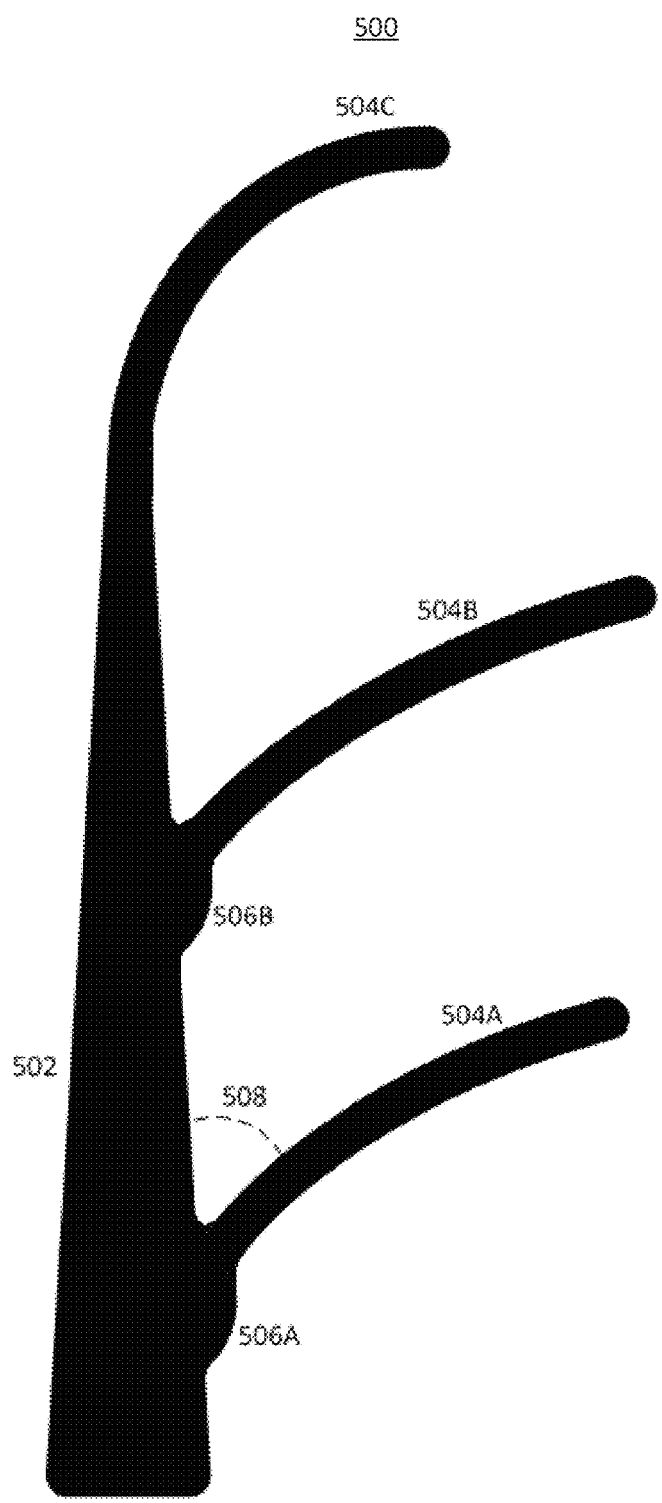
FIG. 5 is a schematic view of a network of channels.

FIG. 5 depicts a network of channels 500 for transporting fluid. The network 500 includes a trunk channel 502 and branch channels 504A-C. The branch channels 504A and 504B include low pressure zones 506A and 506B, respectively. In one implementation, the network 500 represents the network of channels within the blood substrate layer 200 shown in FIG. 2. For example, the trunk 502 of FIG. 5 corresponds to the primary channel 202 of FIG. 2, and the branch channels 504A-504C correspond to the secondary channels 204 of FIG. 2. The network of channels 500 can also represent the channels in the manifolds 110, 112, 114, and 116 and bilayers 102 of FIG. 1A. For example, the trunk 502 can represent the primary channel 118 and the branches 504A-504C can represent the secondary channels 120 of the blood inlet manifold 110.

In one implementation, a volume of fluid enters the trunk 502 at its widest point. The fluid travels along the trunk 502 and is redirected through the branch channels 504A-504C. Low pressure zones 506A and 506B facilitate redirection of fluid from the trunk 502 into the branch channels 504A and 504B. The low pressure zones 506A and 506B are located at the junction of the trunk 502 and the branch channels 504A and 504B. Low fluid pressure is created by increasing the diameter of the branch channels 504A and 504B at the junction point relative to the diameter of the downstream portion of the branch channels 504A and 504B. Fluid flowing through the trunk is more easily redirected into the branch channels 504A and 504B due to the low pressure zones 506A and 506B. As depicted in FIG. 5, the low pressure zones 506A and 506B have a rounded shape.

The angle of the junction between the branch channels 504A-504C and the trunk 502 is selected to allow for smooth flow of fluid from the trunk 502 into the branch channels 504A-C. As shown in the FIG. 5, the angle 508 formed by the junction of the branch channel 504A and the trunk 502, and measured proximate to the junction, is acute. In some implementations, the network of channels 500 is designed so that the angle 508 measures less than about 60°. A smaller value for angle 508 allows fluid flow to avoid turning at a sharp angle as fluid is redirected from the trunk 502 into the branch channel 504A. Such a configuration helps to maintain the wall shear rate within a specified range, which can be useful if the fluid is shear sensitive (e.g., blood).

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed only in connection with one implementation are not intended to be excluded from a similar role in other implementations.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A microfluidic device for processing blood comprising:
 a first network of channels having a plurality of First Channels, each First Channel having a height in the range of about 50 microns to about 500 microns;
 a second network of channels having at least one Second Channel complementary to one or more of the First Channels;
 wherein the plurality of First Channels further comprises:
  an input channel forming a primary channel, a plurality of secondary channels, and an outlet channel wherein
   a width of the primary channel varies along the length of the primary channel such that an angle formed by a centerline of the primary channel and a wall of the primary channel is greater than zero degrees and less than or equal to about 45 degrees;
   a first secondary channel connects to the primary channel at a first junction located at a first distance from a first end of the primary channel;
   a second secondary channel connects to the primary channel at a second junction located at a second distance, greater than the first distance, from the first end of the primary channel;
   at least one of the first and second secondary channels includes a curved portion directing flow away from the primary channel, the curved portion having a radius of curvature that is not less than its hydraulic diameter; and
   at least one of the first and second secondary channels bifurcates into first and second tertiary channels at a third junction.

2. The microfluidic device of claim 1, further comprising a filtration membrane separating a portion of the first network of channels from a portion of the second network of channels.

3. The microfluidic device of claim 1, wherein the plurality of First Channels is located within a first substrate.

4. The microfluidic device of claim 3, wherein the first substrate has a thickness of no less than 10 microns and no greater than 10 millimeters.

5. The microfluidic device of claim 1, wherein the width of the primary channel varies smoothly along the length of the primary channel.

6. The microfluidic device of claim 1, further comprising a flow divider for dividing fluid flow between the first and second tertiary channels, wherein the flow divider has a curved surface connecting to the walls of the first and second tertiary channel, and the radius of curvature of the flow divider is not greater than the hydraulic diameter of the at least one secondary channel.

7. The microfluidic device of claim 1, wherein an angle formed by a centerline of at least one of the secondary channels and a downstream portion of the centerline of the primary channel measures between one and sixty degrees.

8. The microfluidic device of claim 1, wherein the walls of the primary channel are disposed at an angle of no greater than thirty degrees with respect to the direction of fluid flow through the primary channel.

* * * * *